United States Patent
Hwang et al.

(10) Patent No.: US 11,053,275 B2
(45) Date of Patent: Jul. 6, 2021

(54) METHOD FOR BILE ACID DERIVATIVE BY USING CONTINUOUS FLOW REACTION

(71) Applicant: DAEWOONG BIO INC., Hwaseong-si (KR)

(72) Inventors: Tae Seop Hwang, Cheonan-si (KR); Phil Goo Kang, Hwaseong-si (KR); Joon Hwan Lee, Suwon-si (KR); Jin Yong Eo, Suwon-si (KR); Seung Jae Lee, Daejeon (KR)

(73) Assignee: DAEWOONG BIO INC., Hwaseong-si (KR)

(*) Notice: Subject to any disclaimer, the term of this patent is extended or adjusted under 35 U.S.C. 154(b) by 0 days.

(21) Appl. No.: 16/606,446

(22) PCT Filed: Apr. 20, 2018

(86) PCT No.: PCT/KR2018/004639
§ 371 (c)(1),
(2) Date: Oct. 18, 2019

(87) PCT Pub. No.: WO2018/194426
PCT Pub. Date: Oct. 25, 2018

(65) Prior Publication Data
US 2020/0283470 A1     Sep. 10, 2020

Related U.S. Application Data

(60) Provisional application No. 62/487,870, filed on Apr. 20, 2017.

(51) Int. Cl.
*C07J 9/00* (2006.01)

(52) U.S. Cl.
CPC ..................... *C07J 9/005* (2013.01)

(58) Field of Classification Search
CPC ........................................................ C07J 9/005
See application file for complete search history.

(56) References Cited

U.S. PATENT DOCUMENTS 4,792,620 A * 12/1988 Paulik .............. B01J 31/0231
  560/232
4,834,919 A * 5/1989 Magni .................. C07J 9/005
  552/505

FOREIGN PATENT DOCUMENTS

| | | |
|---|---|---|
| CN | 102070693 A | 5/2011 |
| CN | 105315320 A | 2/2016 |
| CN | 105418712 | 3/2016 |
| CN | 106046095 A | 10/2016 |
| EP | 0230085 A1 | 7/1987 |
| EP | 3287467 A1 | 2/2018 |
| FR | 2653129 A1 | 4/1991 |
| JP | S5639100 A | 4/1981 |
| JP | S57-56497 A | 4/1982 |
| JP | 2-282393 A | 11/1990 |
| JP | H0532692 A | 2/1993 |
| JP | 05-059093 A | 3/1993 |
| WO | 200062919 A | 10/2000 |
| WO | 2006010490 A1 | 2/2006 |
| WO | 2006122977 A2 | 11/2006 |
| WO | 2007112945 A1 | 10/2007 |
| WO | 2013192097 A1 | 12/2013 |
| WO | 2017019524 A1 | 2/2017 |

OTHER PUBLICATIONS

Norskov et al, Nature Chemistry, Towards the Computational Design of Solid Catalysts, 2009, 1, pp. 37-46. (Year: 2009).*
Irfan et al, ChemSusChem, Heterogeneous Catalytic Hydrogenation Reactions in Continuous-Flow Reactors, 2011, 4(3), pp. 300-316. (Year: 2011).*
International Search Report issued by the International Searching Authority (ISA/KR) in Application No. PCT/KR2018/004639 dated Jul. 31, 2018. English Translation. 3 pages.
Tian, He, Hongbin Zhao, and Xuejun Cao. "Catalytic transfer hydrogenation of 7-ketolithocholic acid to ursodeoxycholic acid with Raney nickel." Journal of Industrial and Engineering Chemistry 19.2 (2013): 606-613.
Japanese Office Action relating to Japanese Application No. 2020-507973, dated Aug. 31, 2020.
European Search Report relating to Application No. 18786942.5, dated Nov. 23, 2020.

* cited by examiner

*Primary Examiner* — Sikarl A Witherspoon
(74) *Attorney, Agent, or Firm* — Meunier Carlin & Curfman LLC

(57) ABSTRACT

Provided herein is a method of preparing a bile acid derivative using a continuous flow reaction. When bile acid derivatives are synthesized using a continuous flow reaction according to the present invention, the reaction is very safe compared to an existing batch-type reaction, the reaction time is significantly reduced, and high-quality bile acid derivatives may be synthesized with high efficiency. In particularly, according to the present invention, a hydrogenation reaction proceeds under substantially water-free reaction conditions, and thus the conversion rate (UDCA: CDCA) of a UDCA hydrogenation reaction may be significantly enhanced.

11 Claims, No Drawings

METHOD FOR BILE ACID DERIVATIVE BY USING CONTINUOUS FLOW REACTION

CROSS-REFERENCE TO RELATED APPLICATIONS

This application is a national stage application filed under 35 U.S.C. § 371 of PCT/KR2018/004639 filed Apr. 20, 2018, which claims the benefit of and priority to U.S. Patent Application No. 62/487,870 filed on Apr. 20, 2017, the disclosure of which is expressly incorporated herein by reference in its entirety.

TECHNICAL FIELD

The present invention relates to a method of preparing a bile acid derivative using a continuous flow reaction.

BACKGROUND ART

Bile acid derivatives are prepared by a process of reducing a starting material having a ketone group to a bile acid derivative having a hydroxyl group through a hydrogenation reaction. Conventionally, processes of reducing such ketone groups using metal Na have been performed, but techniques for synthesizing bile acid derivatives using metal Na are dangerous due to the intrinsic risk of explosion. In addition, techniques for synthesizing bile acid derivatives through a hydrogenation reaction using a metal catalyst are also known, but have not yet overcome safety problems.

Meanwhile, a continuous flow reaction is a method of inducing a reaction by continuously supplying a small amount of a reaction sample into a reactor, unlike a batch reaction. When the reaction progresses using such continuous flow, high-risk reactions, for example, a hydrogenation reaction, a cryogenic reaction, a high-temperature reaction, an oxidation reaction, a reduction reaction, and the like, may be carried out with high efficiency. When the continuous flow reaction is used, a significant decrease in reaction time and highly efficient synthesis of drug substances are possible due to excellent mixing efficiency and excellent heat transfer efficiency, compared to a basic batch reaction.

DISCLOSURE

Technical Problem

The inventors of the present invention aim to provide a technique capable of satisfying yield, quality, and the like, and safely synthesizing bile acid derivatives.

Technical Solution

Therefore, the present invention provides a novel method of preparing a bile acid derivative through a continuous flow reaction.

In the present invention, the bile acid derivative may be a compound represented by Formula 1:

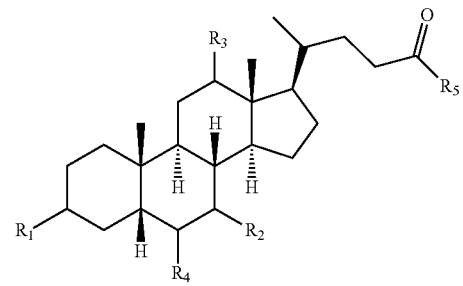

[Formula 1]

wherein, in Formula 1,
$R_1$ to $R_3$ are each independently C=O, α-OH, β-OH, or H,
$R_4$ is H or an α-$C_{1-6}$ alkyl,
$R_5$ is OH or $NHCH_2COOH$ and
at least one of $R_1$ to $R_3$ is α-OH or β-OH.

The compound of Formula 1 may be obtained by reducing a compound having a ketone group and represented by Formula 2:

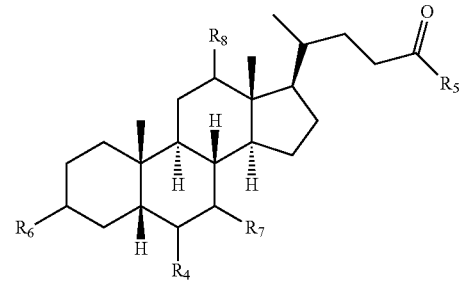

[Formula 2]

wherein, in Formula 2,
$R_6$ to $R_8$ are each independently C=O, α-OH, β-OH, or H,
$R_4$ is H or an α-$C_{1-6}$ alkyl,
$R_5$ is OH or $NHCH_2COOH$, and
at least one of $R_6$ to $R_8$ is C=O, wherein the at least one C=O of $R_6$ to $R_8$ is reduced to α-OH or β-OH through a hydrogenation reaction.

The present invention provides a method of preparing a compound represented by Formula 1, comprising subjecting a compound represented by Formula 2 to a hydrogenation reaction in the presence of a metal catalyst through continuous flow synthesis under substantially water-free reaction conditions.

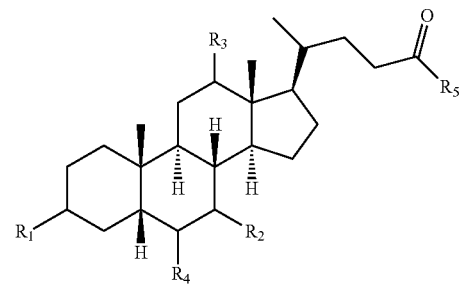

[Formula 1]

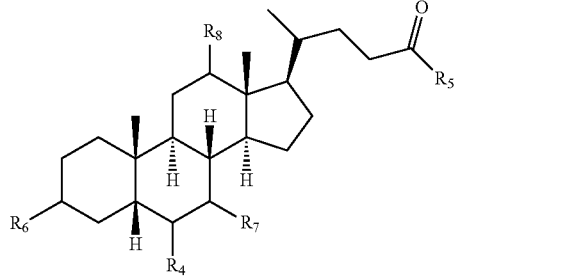

[Formula 2]

wherein, in Formulae 1 and 2, $R_1$ to $R_3$ are each independently C=O, α-OH, β-OH, or H, $R_4$ is H or an α-$C_{1-6}$ alkyl, $R_5$ is OH or $NHCH_2COOH$, and at least one of $R_1$ to $R_3$ is α-OH or (β-OH, $R_6$ to $R_8$ are each independently C=OH, α-OH, β-OH, or H, and at least one of $R_6$ to $R_3$ is C=O, wherein the at least one C=O of $R_6$ to $R_8$ is reduced to α-OH or β-OH through a hydrogenation reaction.

In the present invention, it is important to synthesize the compound of Formula 1 by subjecting the compound of Formula 2 to a hydrogenation reaction in the presence of a metal catalyst through continuous flow synthesis under substantially water-free reaction conditions. As can be confirmed from the following comparative example, when a hydrogenation reaction is carried out in a conventional batch-type reactor, the conversion rate of a UDCA hydrogenation reaction was not good even when the hydrogenation reaction is performed using the same type of metal catalyst as that used in the present invention, and the yield of a related impurities such as chenodeoxycholic acid (CDCA) was high. In contrast, in the following examples of the present invention, the hydrogenation reaction was performed under substantially water-free reaction conditions, thereby increasing the conversion rate (UDCA: CDCA) of the UDCA hydrogenation reaction up to 92% to 97%.

The term "substantially water-free reaction conditions" refers to, for example, a moisture content of less than 5% (w/v) under reaction conditions. As used herein, the term "moisture content under reaction conditions" refers to a moisture content in materials added into reactor for the hydrogenation reaction, including a starting material, a solvent, and/or a catalyst, for example, in 1 L of a reactant solution. Preferably, the moisture content under reaction conditions is less than 3% (w/v), 2% (w/v), or 1% (w/v). More preferably, the moisture content under reaction conditions is less than 1% (w/v), for example, less than 0.5% (w/v), 0.1% (w/v), 0.05% (w/v), or 0.01% (w/v).

In one embodiment of the present invention, in Formulae 1 and 2, $R_1$ and $R_3$ are each independently C=O, α-OH, β-OH, or H, $R_2$ is α-OH or β-OH, $R_4$ is H or an α-$C_{1-6}$ alkyl, $R_5$ is OH or $NHCH_2COOH$, $R_6$ and $R_8$ are each independently C=O, α-OH, β-OH, or H, $R_7$ is C=O, and at least one C=O of $R_6$ to $R_8$ is reduced to α-OH or β-OH through the hydrogenation reaction.

In one embodiment of the present invention,

The compound of Formula 1 may be a compound of Formula 1a below, and the compound of Formula 2 may be a compound of Formula 2a below:

[Formula 1a]

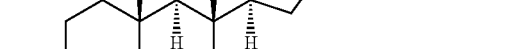

[Formula 2a]

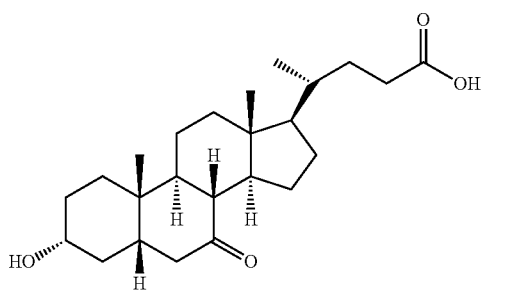

The compound of Formula 1 according to the present invention may be synthesized by performing a hydrogenation reaction while flowing a reactant solution, which is prepared by dissolving the compound of Formula 2 in a protic solvent, and hydrogen into a reactor including a continuous flow channel.

The compound of Formula 2 is used as a starting material of a continuous flow reaction, and to introduce it into the reactor including a continuous flow channel, it is required to dissolve the compound of Formula 2 in a solvent.

In this regard, a protic solvent may be used as a solvent used to dissolve the compound of Formula 2. For example, the solvent may be, but is not limited to, an alcohol, a dialkyl ketone (R=C1 to C4), tetrahydrofuran, dichloromethane, 1,4-dioxane, or a mixture thereof.

In one embodiment of the present invention, the protic solvent may be a $C_{1-6}$ alcohol. For example, the $C_{1-6}$ alcohol may be methanol, ethanol, isopropyl alcohol, butyl alcohol, or the like.

The concentration of the compound of Formula 2 dissolved in the protic solvent may range from, but is not limited to, 0.005% (w/v) to 5% (w/v), for example, 0.01% (w/v) to 2% (w/v), 0.01% (w/v) to 1% (w/v), 0.01% (w/v) to 0.5% (w/v), or 0.02% (w/v) to 0.2% (w/v).

The reactant solution comprises a base, in addition to the compound of Formula 2. The base may be, but is not limited to, KOH NaOH, Kt-OBu, $K_2CO_3$, $Na_2CO_3$, or the like. Preferably, the base is KOH, NaOH, or Kt-OBu.

The base used in the present reaction acts as a reaction initiator. Although not bound by theory, the base acts on the compound of Formula 2 having an aliphatic ketone structure to form an enolate structure, and the compound of Formula 2 having the enolate structure is synthesized into the compound of Formula 1 having an OH group by the action of a catalyst. In this regard, the compound of Formula 1 (product) has the same steric structure as that of the compound of Formula 2 (starting material).

The purity and reaction time of reactants may vary depending on the amount of base used in the present invention. Considering these factors, one of ordinary skill in the art may arbitrarily select an appropriate amount of the base. In this regard, the concentration of the compound of Formula 2, the concentration of the base, and the amount of the solvent used are comprehensively considered. Generally, the amount of the base used in the present invention ranges from 1 equivalent to 10 equivalents, preferably 1 equivalent to 3 equivalents.

Thus, the protic solvent used to dissolve the compound of Formula 2 may also be substantially free of water. For example, the protic solvent may have a purity of 95% (w/v) or more, and the content of moisture in the protic solvent may be less than 5% (w/v). Preferably, the purity of the protic solvent may be 99% (w/v) or more, and the content of moisture in the protic solvent may be less than 0.1% (w/v).

In the present invention, the reactor used in the continuous flow reaction includes a continuous flow channel.

The reactor including a continuous flow channel may be divided into a fixed-bed flow reactor or a moving-bed flow reactor according to the method of adding a catalyst. Processes of the hydrogenation reaction after catalyst addition are carried out in the same manner in the two types.

In the fixed-bed flow reactor, a reaction proceeds while a reactant solution passes through a cartridge column for a continuous flow reaction which is filled with a catalyst. Specifically, a cartridge column is filled with a catalyst and washed with a solvent to remove water, and then the temperature of the cartridge column is raised, hydrogen is supplied through the cartridge column to reach a hydrogen saturated state, and then a reaction solution is allowed to flow into the cartridge column.

The moving-bed flow reactor uses a method wherein a catalyst is introduced into a continuous flow reactor along with a reactant solution without being immobilized on a cartridge column. In the continuous flow reactor, a catalyst is added to a reactant solution (i.e., a mixture of a starting material, a base, and a solvent) and uniformly mixed. For a hydrogenation reaction to progress, the temperature of the reactor is raised, hydrogen is allowed to pass through the reactor, and then the reactant solution is allowed to flow thereinto.

The fixed-bed flow reactor and the moving-bed flow reactor, which may be used for the continuous flow reaction, are well known in the art, and the type of reactor that may be used in the present invention is not particularly limited. reactor having a shape and internal structure suitable for the synthesis of the compound of Formula 1 of the present invention may be selected by one of ordinary skill in the art.

In one embodiment of the present invention, the reactor including a continuous flow channel may be a fixed-bed flow reactor. In the examples described below, a reaction was carded out using a fixed-bed flow reactor, thereby obtaining a product with excellent yield and excellent quality.

The fixed-bed flow reactor may be, but is not limited to, a cylindrical type column reactor. The fixed-bed flow reactor may be, but is not limited to, for example, a CSTR, a multitubular reactor, a multibed reactor, a fluidized-bed reactor, a tray-column reactor, or the like, according to the type of internal structure thereof. The type of suitable fixed-bed flow reactor is not particularly limited, but in one embodiment of the present invention, a multibed reactor may be used as the fixed-bed flow reactor.

Meanwhile, an internal pressure of the reactor may range from 1 atm to 100 atm. The internal pressure of the reactor may affect reaction time and reaction quality. The internal pressure of the reactor may range from, but is not limited to, for example, 1 atm to 50 atm, 1 atm to 30 atm, 1 atm to 20 atm, or 1 atm to 10 atm. In a specific example of the present invention, the internal pressure of the reactor may be adjusted to, for example, 3 atm to 6 atm or 4 atm to 5 atm.

When flowing, into the reactor, the reactant solution prepared by dissolving the compound of Formula 2 in a protic solvent, an appropriate rate may be given.

Although not being limited thereto, in a specific embodiment of the present invention, the reactant solution may be introduced into the reactor at a flow rate of 30 µl/ml to 200 µl/ml.

The flow rate of the reactant solution may vary depending on the type of reactor to be used, i.e., whether the reactor is a fixed-bed flow reactor or a moving-bed flow reactor. For example, when the fixed-bed flow reactor is used, the flow rate of the reactant solution may range from, for example, 20 µl/min to 100 µl/min, 30 µl/min to 90 µ/min, 40 µl/min to 80 µl/min, or 50 µl to 60 µl/min. When the moving-bed flow reactor is used, the flow rate of the reactant solution may range from, for example, 70 µl/min to 130 µl/min, 80 µl/min to 120 µl/min, or 90 µl/min to 110 µl/min.

To subject the compound of Formula 2 included in the reactant solution to a hydrogenation reaction, hydrogen is also introduced into the reactor.

Although not being limited thereto, hydrogen is introduced into the reactor at a flow rate of 1 ml/min to 10 µl/min. For example, the flow rate of hydrogen may be adjusted to between 3 ml/min and 8 ml/min, or between 4 ml/min and 6 ml/min. in this case, a hydrogen supply pressure in the reactor may range from, for example, 1 bar to 10 bar, 2 bar to 8 bar, 3 bar to 6 bar, for example, 5 bar or 3 bar.

Additionally, a distributor may be attached to an inlet of the reactor to appropriately adjust an inflow/discharge amount in the reactor or uniformly maintain the time taken for the starting material to pass through the reactor so that a starting material first introduced into the reactor is discharged as a product, and then discharge of a starting material introduced thereafter follows.

Meanwhile, in the present invention, a catalyst used for the hydrogenation reaction may affect reaction yield and a reaction rate.

While metal Na is used as a catalyst in conventional methods of producing bile acid derivatives, a metal catalyst is used in the present invention.

In the present invention, the metal catalyst enables hydrogen molecules to be converted into radical ions. Although not being in accordance with any theory, according to the research results of the inventors of the present invention, the compound of Formula 2 having an aliphatic ketone structure forms an enolate structure under base conditions. The compound of Formula 2 having an enolate structure is synthesized into the compound of Formula 1 having an OH group by action of a catalyst and an activated hydrogen radical ion on the surface of the catalyst. in this regard, the compound of Formula 1 (product) has the same steric structure as that of the compound of Formula 2 (starting material).

In the present invention, the metal catalyst may be selected from the group consisting of Pd, Rh, Ru, Pt, Ni, Pd/C, a Ni—Al alloy catalyst, and a Raney-Ni catalyst. In one embodiment of the present invention, the metal catalyst may be Pd/C or a Ni—Al alloy catalyst. Preferably, the metal catalyst may be a Raney-Ni catalyst. In particular, examples of catalysts suitable for use in the moving-bed flow reactor include a ruthenium catalyst, a rhodium catalyst, or a homogenous catalyst consisting of a mixture thereof.

Although not being limited thereto, the compound of Formula 2 as a starting material and the catalyst may be used in a weight ratio of 1:0.3 to 0.9, for example, 1:04 to 0.8, or 1:0.5 to 0.7.

As described above, in the synthesis reaction of the compound of Formula 1 according to the present invention, it is important to maintain substantially water-free conditions. Thus, it is important that water is not contained in the entire reaction process regardless of the type of catalyst used. In most cases, metal catalysts are usually provided with water due to reactivity thereof. Therefore, to embody the present invention, it is important to wash a metal catalyst with a substantially water-free solvent (e.g., the protic solvent used in the reactant solution) before the metal catalyst is used in the hydrogenation reaction so that the metal catalyst is substantially free of water.

In the present invention, a reaction temperature for the hydrogenation reaction may range from, but is not limited to, 10° C. to 90° C. In one embodiment of the present invention, the reaction temperature for the hydrogenation reaction may range from, for example, 20° C. to 80° C. 30° C. to 70° C., or 40° C. to 60° C.

Advantageous Effects

When bile acid derivatives are synthesized using a continuous flow reaction according to the present invention, the reaction is very safe compared to an existing batch-type reaction, the reaction time is significantly reduced to a level of ⅕ or less, and high-quality bile acid derivatives can be synthesized with high efficiency. In particularly, according to the present invention, a hydrogenation reaction proceeds under substantially water-free reaction conditions, and thus the conversion rate (UDCA: CDCA) of a UDCA hydrogenation reaction can be significantly enhanced to a level of 92:3 (a ratio of UDCA to CDCA) compared to an existing level of about 83:17.

MODE OF THE INVENTION

Advantages and features of the present invention and methods for achieving them will become apparent with reference to the examples described below in detail. However, the present invention is not limited to the examples disclosed below, but may be embodied in various different forms. Rather, the present examples are provided so that this disclosure will be complete and will fully convey the scope of the invention to those of ordinary skill in the art to which the present invention pertains. In addition, the present invention should be defined by the scope of the appended claims.

EXAMPLES

Example 1

A cartridge column for a continuous flow reaction was filled with 0.67 g of a palladium hydroxide catalyst and washed with isopropyl alcohol to remove water contained in the catalyst. 1.0 g of 7-keto-lithocholic acid (KLCA) as a starting material and 144 mg of KOH were well dissolved in 50 mL of isopropyl alcohol, and then 144 mg of tert-BuOK was added thereto and the resulting solution was stirred at room temperature for 10 minutes.

The temperature of the cartridge column was raised to 40° C., hydrogen was supplied thereinto at a flow rate of 5 mL/min, and the reaction solution was allowed to flow thereinto at a flow rate of 100 μL/min, to perform a hydrogenation reaction. The temperature of the catalyst column was raised to 80° C. at a hydrogen flow rate of 5 ml/min, and the flow rate of the reaction solution was fixed at 60 μL/min to perform the hydrogenation reaction.

At the time of reaction completion, ursodeoxycholic acid (UDCA) was produced with a yield of 95% within several minutes, and the obtained conversion rate (UDCA: CDCA) of the UDCA hydrogenation reaction was 92% to 97%.

Example 2

A cartridge column for a continuous flow reaction was filled with 0.67 g of a Raney Ni catalyst and water was removed therefrom using isopropyl alcohol. 1.0 g of KLCA as a starting material and 144 mg of KOH were well dissolved in 50 mL of isopropyl alcohol, and then the 144 mg of t-BuOK was added thereto and the resulting solution was stirred at room temperature for 10 minutes.

The temperature of the cartridge column was raised to 40° C., hydrogen was supplied thereinto at a flow rate of 5 mL/min, and the reaction solution was allowed to flow thereinto at a flow rate of 60 μL/min, to perform a hydrogenation reaction. The temperature of the catalyst column was raised to 80° C. at a hydrogen flow rate of 5 mL/min, and the flow rate of the reaction solution was fixed at 60 μL/min to perform the hydrogenation reaction At the time of reaction completion, UDCA was produced with a yield of 95% within several minutes, and the obtained conversion rate (UDCA: CDCA) of the UDCA hydrogenation reaction was 92% to 97%.

Example 3

In a general reactor, 1.0 g of KLCA as a starting material and 144 mg of KOH were well dissolved in 50 mL of isopropyl alcohol, and then 144 mg of t-BuOK was added thereto and the resulting solution was stirred at room temperature for 10 minutes. 0.67 g of a palladium hydroxide catalyst was washed with 10 ml of isopropyl alcohol in a nitrogen atmosphere and filtered, and this process was repeated three times. Lastly, the palladium hydroxide catalyst, which became wet due to the isopropyl alcohol, was added to the reaction solution and uniformly mixed. The temperature of the continuous flow reactor was raised to 40° C. The reaction solution was allowed to flow into the first line of the continuous flow reactor at a flow rate of 100 μL/min, and hydrogen was supplied into the second line thereof at a flow rate of 5 mL/min and a pressure of 5 bar to perform a hydrogenation reaction. After the reaction was completed, the catalyst was filtered. At the time of reaction completion, UDCA was produced with a yield of 95% within several minutes, and the obtained conversion rate (UDCA: CDCA) of the UDCA hydrogenation reaction was 92% to 97%.

Example 4

In a general reactor, 1.0 g of KLCA as a starting material and 144 mg of KOH were well dissolved in 10 mL of isopropyl alcohol, and then 144 mg of tert-BuOK was added thereto and the resulting solution was stirred at room temperature for 10 minutes. 0.67 g of a Raney Ni catalyst was washed with 10 ml of isopropyl alcohol in a nitrogen atmosphere and filtered, and this process was repeated three times. Lastly, the Raney Ni catalyst, which became wet due to the isopropyl alcohol, was added to the reaction solution and uniformly mixed. The temperature of the continuous flow reactor was raised to 40° C. The reaction solution was allowed to flow into the first line of the continuous flow reactor at a flow rate of 100 μL/min, and hydrogen was supplied into the second line thereof at a flow rate of 5 mL/min and a pressure of 5 bar to perform a hydrogenation reaction. After the reaction was completed, the catalyst was filtered. At the time of reaction completion, UDCA was produced with a yield of 95% within several minutes, and the obtained conversion rate (UDCA: CDCA) of the UDCA hydrogenation reaction was 92% to 97%.

Example 5

In a general reactor, 1.0 g of KLCA as a starting material and 144 mg of KOH were well dissolved in 50 mL of isopropyl alcohol, and then 144 mg of tert-BuOK was added thereto and the resulting solution was stirred at room temperature for 10 minutes. 0.67 g of a palladium carbon catalyst was washed with 10 mL of isopropyl alcohol in a nitrogen atmosphere and filtered, wherein this process was repeated three times, and the palladium carbon catalyst, which became wet due to the isopropyl alcohol, was added to the reaction solution and uniformly mixed. The temperature of the continuous flow reactor was set at 40° C. and raised to the temperature. The reaction solution was allowed to flow into the first line of the continuous flow reactor at a flow rate of 100 μL/min, and hydrogen was uniformly supplied into the second line thereof while maintaining a hydrogen flow rate at 5 mL/min and a hydrogen pressure at 5 bar. After the reaction was completed, the catalyst was filtered. At the time of reaction completion, UDCA was produced with a yield of 95% within several minutes, and the obtained conversion rate (UDCA: CDCA) of the UDCA hydrogenation reaction was 92% to 97%.

Example 6

A cartridge column for a continuous flow reaction was filled with 0.67 g of palladium carbon (Pd/C) and water was removed therefrom with isopropyl alcohol. 1.0 g of KLCA as a starting material and 144 mg of KOH were well dissolved in 50 mL of isopropyl alcohol, and then 144 mg of tert-BuOK was added thereto and the resulting solution was stirred at room temperature for 10 minutes. The temperature of the cartridge column was raised to 40° C., hydrogen was supplied thereinto at a flow rate of 5 ml/min, and the reaction solution was allowed to flow thereinto at a flow rate of 100 μL/min, to perform a hydrogenation reaction. The temperature of the catalyst column was raised to 80° C. at a hydrogen flow rate of 5 ml/min, and the flow rate of the reaction solution was fixed at 60 μL/min to perform the hydrogenation reaction. At the time of reaction completion, UDCA was produced with a yield of 95% within several minutes, and the obtained conversion rate (UDCA: CDCA) of the UDCA hydrogenation reaction was 92% to 97%.

Representatively, the experimental conditions and results of Example 4 are shown in the following table.

Flow Type Hydrogen Reactor Used—Lab Test Results

| Entry | Solvent | g/mL Concentration | ° C. Temperature | mL/min Hydrogen | Bar Back pressure regulator (BPR) | μL/min Flow rate | Retention time 12.47 Iso-UDCA (related impurities) |
|---|---|---|---|---|---|---|---|
| 1 | IPA | 0.1 | 100 | 5 | 3 | 100 | 1.57 |
| 2 | IPA | 0.1 | 100 | 5 | 3 | 100 | 1.07 |
| 3 | IPA | 0.1 | 100 | 5 | 3 | 100 | 1.85 |

| Entry | Retention time 14.43 UDCA | Retention time 18.8 KLCA | Retention time 41.08 CDCA | Reactivity 100%-starting material | Conversion rate U/C(95/5) 19 or more | Reaction time Batch 8 hr |
|---|---|---|---|---|---|---|
| 1 | 92.09 | 0.04 | 3.54 | 99.6% | 26 | 1.6 hr |
| 2 | 91.56 | 0.04 | 3.98 | 99.6% | 23 | 1.6 hr |
| 3 | 91.47 | 0 04 | 3.58 | 99.6% | 25.5 | 1.6 hr |

In the above table, reactivity refers to the completeness of the reaction, which is calculated by subtracting an unreacted percentage from the total 100%, and the conversion rate refers to a ratio of UDCA to CDCA. As can be seen in the above table, according to the present invention, it can be seen that the conversion rate is obtained at a ratio of 95:5 or higher (a value of U/C of 19 or more). Reaction time is calculated by dividing 10 mL. (amount of reaction solution) by (0.1 L/min (100 μL)×60 min).

Comparative Example

A UDCA hydrogenation reaction was carried out using KLCA as a starting material in the presence of a Raney-Ni catalyst using a batch-type hydrogenation reactor under the following conditions.

Batch Reaction Results

| Catalyst/hydrogen pressure | Solvent | Amount of solvent | Amount of catalyst | Temperature | Reaction time | Reactivity | Unreacted | Conversion rate (UDCA:CDCA) | Iso-CDCA (related impurities) |
|---|---|---|---|---|---|---|---|---|---|
| Raney-Ni/ hydrogen pressure 5 atm | Isopropyl alcohol | 50 vol | 1 vol | 70° C. | 5.5 hr | 76% | 24% | 68:05 (13.6) | 2.2% |
| | | 50 vol | 1 vol | 78° C. | 5.5 hr | 98% | 2% | 87:06 (14.5) | 4.0% |
| | | 50 vol | 1 vol | 78° C. | 3.5 hr | 87% | 13% | 78:05 (15.6) | 3.1% |
| | | 50 vol | 1 vol | 78° C. | 24 hr | 100% | N/D | 84:05 (16.8) | 9.0% |
| | | 50 vol | 1 vol | 70° C. | 24 hr | 98% | 2% | 86:05 (17.2) | 6.3% |
| | | 25 vol | 1 vol | 78° C. | 5.5 hr | 98% | 2% | 87:06 (14.5) | 4.0% |
| | | 25 vol | 1 vol | 78° C. | 24 hr | 100% | N/D | 84:05 (16.8) | 9.9% |

As can be seen from the above results, in the case of a general reactor, the longer the reaction time, the higher the reactivity, but the conversion rate (UDCA: CDCA) of the UDCA hydrogenation reaction was not high and the yield of related impurities was high, compared to the continuous flow reaction. In addition, in the case of the continuous flow reaction, the reaction time may be significantly reduced to a level of ⅕ or less and the conversion rate may be enhanced, as compared to the batch-type reaction.

The invention claimed is:

1. A method of preparing a compound of Formula 1, the method comprising synthesizing the compound of Formula 1 by subjecting a compound of Formula 2 to a hydrogenation reaction in the presence of a metal catalyst through continuous flow synthesis under substantially water-free reaction conditions:

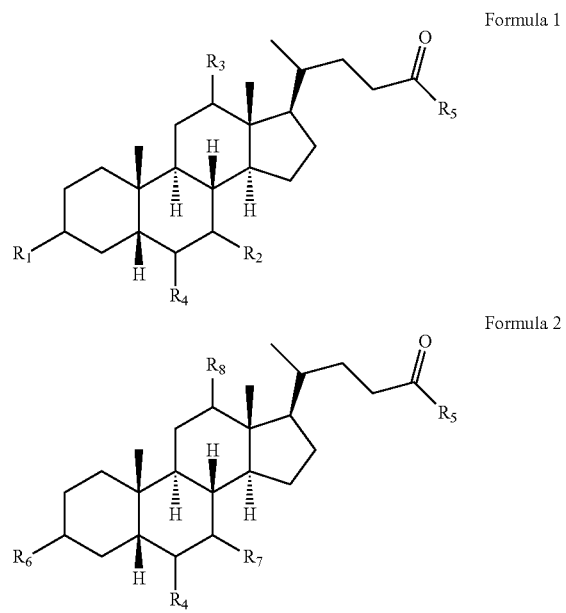

Formula 1

Formula 2 wherein, in Formulae 1 and 2, $R_1$ to $R_3$ are each independently C=O, α-OH, β-OH, or H, $R_4$ is H or an α-$C_{1-6}$ alkyl, $R_5$ is OH or $NHCH_2COOH$, at least one of $R_1$ to $R_3$ is α-OH or β-OH, $R_6$ to $R_8$ are each independently C=O, α-OH, β-OH, or H, $R_4$ is H or an α-$C_{1-6}$ alkyl, $R_5$ is OH or $NHCH_2COOH$, at least one of $R_6$ to $R_8$ is C=O, wherein the at least one C=O of $R_6$ to $R_8$ is reduced to α-OH or β-OH through the hydrogenation reaction, wherein a moisture content under reaction conditions is less than 0.5% (w/v), and the metal catalyst is selected from the group consisting of a palladium hydroxide catalyst, Pd/C catalyst, and a Raney-Ni catalyst.

2. The method of claim 1, wherein, in Formulae 1 and 2, $R_1$ and $R_3$ are each independently C=O, α-OH, β-OH, or H, $R_2$ is α-OH or β-OH, $R_4$ is H or an α-$C_{1-6}$ alkyl, $R_5$ is OH or $NHCH_2COOH$, $R_6$ and $R_8$ are each independently C=O, α-OH, β-OH, or H, and $R_7$ is C=O, wherein at least one C=O of $R_6$ to $R_8$ is reduced to α-OH or β-OH through the hydrogenation reaction.

3. The method of claim 1, wherein the compound of Formula 1 is a compound of Formula 1a below, and the compound of Formula 2 is a compound of Formula 2a below:

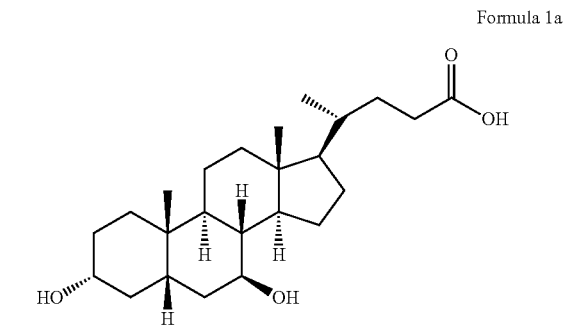

Formula 1a

Formula 2a

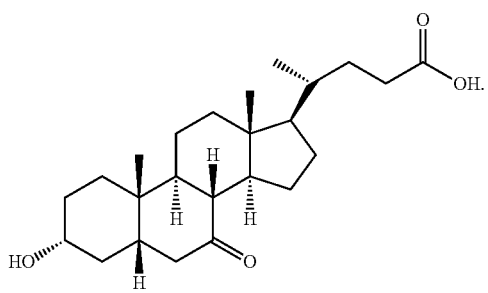

4. The method of claim 1, wherein the synthesizing of the compound of Formula 1 comprises performing a hydrogenation reaction while flowing a reactant solution and hydrogen into a reactor comprising a continuous flow channel, the reactant solution being prepared by dissolving the compound of Formula 2 in a protic solvent.

5. The method of claim 4, wherein the reactor comprising a continuous flow channel is a fixed-bed flow reactor or a moving-bed flow reactor.

6. The method of claim 4, wherein an internal pressure of the reactor ranges from 1 atm to 100 atm.

7. The method of claim 4, wherein the reactant solution is introduced into the reactor at a flow rate of 30 μl/min to 200 μl/min.

8. The method of claim 4, wherein the hydrogen is introduced into the reactor at a flow rate of 1 ml/min to 10 ml/min.

9. The method of claim 1, wherein reaction temperature for the hydrogenation reaction ranges from 10° C. to 90° C.

10. The method of claim 1, wherein the conversion yield of hydrogenation reaction is greater than 92%.

11. The method of claim 1, wherein the conversion yield of hydrogenation reaction is from 92% to 97%.

* * * * *